United States Patent
Yang

(10) Patent No.: US 6,544,222 B1
(45) Date of Patent: Apr. 8, 2003

(54) VISUALIZATION THROUGH AN OPAQUE MEDICAL DEVICE COMPONENT

(75) Inventor: Arlene S. Yang, Redwood City, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 146 days.

(21) Appl. No.: 09/713,747

(22) Filed: Nov. 14, 2000

(51) Int. Cl.[7] ............................................. A61M 29/00
(52) U.S. Cl. .................................. 604/103.01; 604/96
(58) Field of Search ..................... 604/103.01, 103.06, 604/103.1, 103.11, 103.12, 103.13, 915, 917, 102.01, 99.04, 96.01, 95.01

(56) References Cited

U.S. PATENT DOCUMENTS

| | | | | |
|---|---|---|---|---|
| 3,655,129 A | * | 4/1972 | Seiner ........................ | 239/60 |
| 4,917,666 A | * | 4/1990 | Solar et al. .............. | 604/95.01 |
| 5,100,381 A | * | 3/1992 | Burns ..................... | 604/103.01 |
| 5,269,755 A | | 12/1993 | Bodicky ..................... | 604/53 |
| 5,397,305 A | * | 3/1995 | Kawula et al. ........... | 604/96.01 |
| 5,429,605 A | * | 7/1995 | Berad et al. ........... | 604/103.11 |
| 5,454,788 A | * | 10/1995 | Walker et al. .......... | 604/99.04 |
| 5,752,934 A | | 5/1998 | Campbell et al. ............. | 604/96 |
| 5,868,704 A | | 2/1999 | Campbell et al. ............. | 604/96 |
| 6,120,477 A | | 9/2000 | Campbell et al. ............. | 604/96 |
| 6,193,685 B1 | * | 2/2001 | Goodin ................... | 604/102.01 |

* cited by examiner

*Primary Examiner*—Teresa Walberg
*Assistant Examiner*—Leonid Festovsky
(74) *Attorney, Agent, or Firm*—Fulwider Patton Lee & Utecht, LLP

(57) ABSTRACT

A method and medical device component allowing visualization through the opaque material used to form the component. In a method of the invention for visualization through a medical device component formed of a porous opaque material, a fluid is applied to the porous material which has a refractive index substantially similar to the refractive index of the porous material, so that the transparency of the porous material is increased. In one embodiment, the medical device component is a catheter balloon.

20 Claims, 1 Drawing Sheet

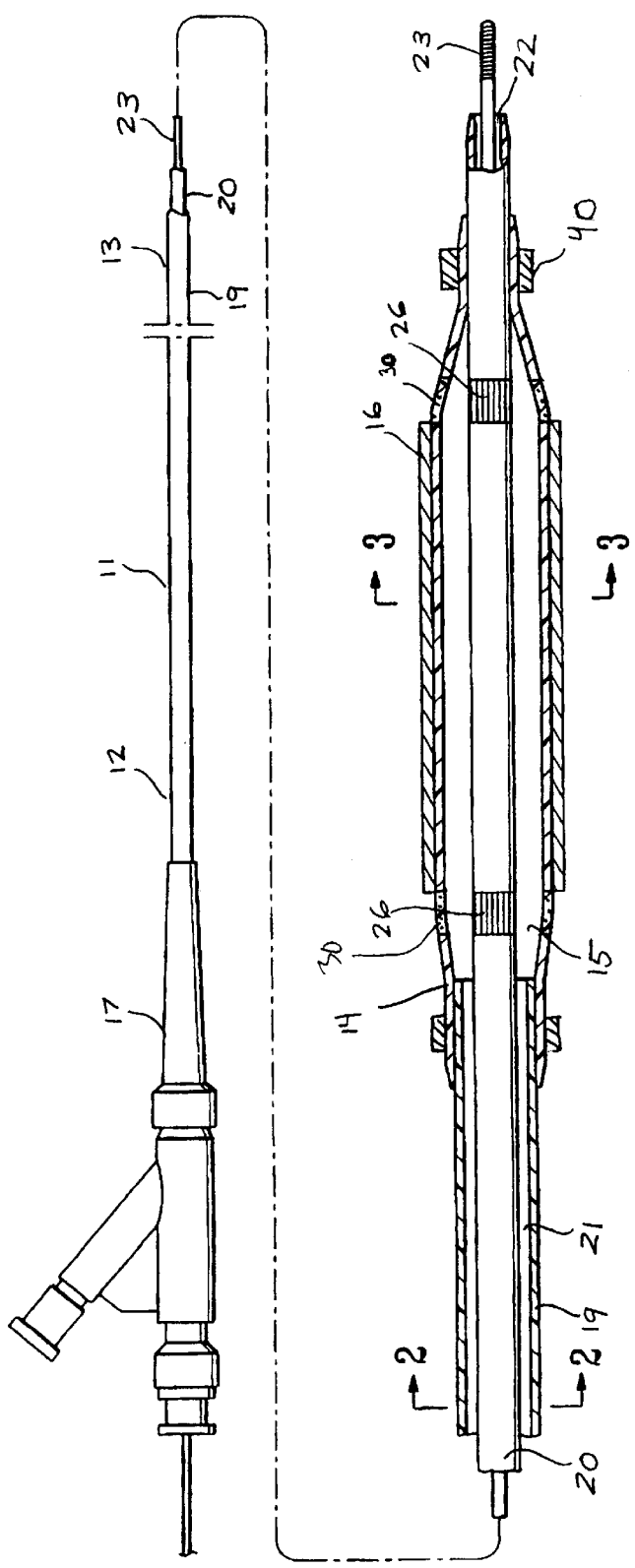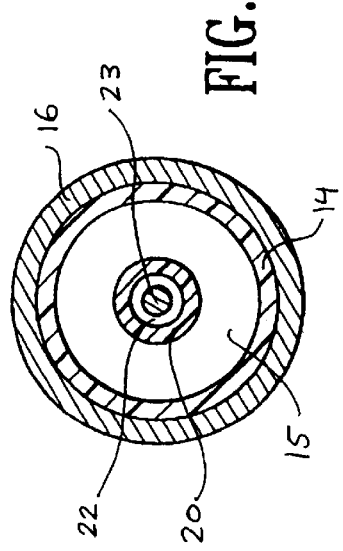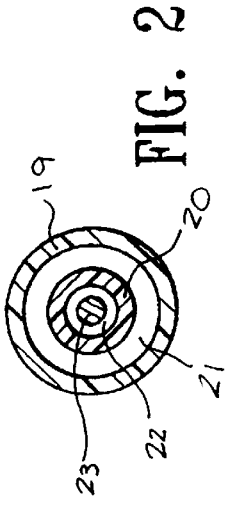

VISUALIZATION THROUGH AN OPAQUE MEDICAL DEVICE COMPONENT

BACKGROUND OF THE INVENTION

This invention generally relates to intravascular catheters, such as balloon catheters used in percutaneous transluminal coronary angioplasty (PTCA).

PTCA is a widely used procedure for the treatment of coronary heart disease. In this procedure, a balloon catheter is advanced into the patient's coronary artery and the balloon on the catheter is inflated within the stenotic region of the patient's artery to open up the arterial passageway and thereby increase the blood flow there through. To facilitate the advancement of the catheter into the patient's coronary artery, a guiding catheter having a preshaped distal tip is first percutaneously introduced into the cardiovascular system of a patient by the Seldinger technique through the brachial or femoral arteries. The guiding catheter is advanced until the preshaped distal tip of the guiding catheter is disposed within the ascending aorta adjacent the ostium of the desired coronary artery, and the distal tip of the guiding catheter is then maneuvered into the ostium. A balloon catheter may then be advanced through the guiding catheter into the patient's coronary artery over a guidewire until the balloon on the catheter is disposed within the stenotic region of the patient's artery.

The balloon is inflated to open up the arterial passageway and increase the blood flow through the artery. Generally, the inflated diameter of the balloon is approximately the same diameter as the native diameter of the body lumen being dilated so as to complete the dilation but not over expand the artery wall. After the balloon is finally deflated, blood flow resumes through the dilated artery and the dilatation catheter can be removed therefrom.

In a large number of angioplasty procedures, there may be a restenosis, i.e. reformation of the arterial plaque in the dilated arterial region. To reduce the restenosis rate and to strengthen the dilated area, physicians now frequently implant an intravascular prosthesis called a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the expanded stent is left in place within the artery.

Radiopaque markers, typically in the form of bands of radiopaque material, are used to mark the working length of the balloon and help physicians to determine the location of the balloon inside a vessel. Radiopaque markers are typically placed on a distal section of the shaft inner tubular member which extends through the interior of the balloon. During assembly of the catheter, the balloon is moved into place over the inner tubular member and the radiopaque markers are visually lined up to correspond with the proximal and the distal ends of the working length of the balloon. Radiopaque markers can also be used to mark the proximal and the distal ends of a stent mounted on the balloon.

Catheter balloons formed of opaque materials such as expanded polytetrafluoroethylene (ePTFE) are not able to be adequately positioned relative to the radiopaque markers due to the inability to visualize the markers through the balloon. Placement of an opaque balloon may be done by referencing the location of the two markers on an outside fixture. However, using outside fixtures for referencing when placing a balloon is not a very accurate technique. Misplacement of the balloon with respect to the radiopaque marker bands may result in later errors in judgement of the balloon location within a patient. What has been needed is a method and a balloon to allow visualization of marker bands through an opaque balloon.

SUMMARY OF THE INVENTION

The present invention is directed to a method and medical device component allowing visualization through the opaque material used to form the component. In a method of the invention for visualization through a medical device; component formed of a porous opaque material, a fluid is applied to the porous material which has a refractive index substantially similar to the refractive index of the porous material, so that the transparency of the porous material is increased.

In a presently preferred embodiment the porous material is expanded polytetrafluoroethylene (ePTFE). The porous ePTFE is opaque due to its porous nature. Specifically, the refractive indexes of the ePTFE and air in the porous ePTFE are sufficiently different to cause the scattering of light waves, thus rendering the ePTFE opaque. In accordance with the invention, the material applied to the porous ePTFE fills the spaces of the ePTFE which would otherwise be filled with air, and has a refractive index substantially similar to that of the ePTFE, so that the ePTFE becomes sufficiently transparent to allow visualization therethrough. In a presently preferred embodiment, the substantially similar refractive index of the material in the pores of the porous material is within about 5% to about 20%, preferably within about 5% to about 10% of the refractive index of the porous material (i.e., the refractive index of the material in the pores is ±5% to ±20% of the refractive index of the porous material).

A variety of suitable materials having a refractive index substantially similar to that of the porous material may be used to increase the transparency of the porous material. In one embodiment, the material in the pores of the porous material is selected from the group consisting of alcohol and silicone. In a presently preferred embodiment, the alcohol is isopropyl alcohol, and the silicone is a silicone-based adhesive such as MED62-15, available from Nusil Technology. In one embodiment, the silicone-based adhesive has an elongation of about 100% to about 600%. A device containing the fluid, such as a pipette, can be used to place the fluid onto the balloon. However a variety of suitable methods can be used to apply the fluid to the porous material, including immersing at least a section, or spraying the fluid on at least a section, of the porous material.

In a presently preferred embodiment, the medical device component is a balloon for a catheter such as an angioplasty catheter or a stent delivery catheter. However, a variety of suitable medical device components formed of porous opaque material may be used including covers for stents or catheter balloons, grafts, and the like. A balloon of the invention formed of a porous opaque material having at least a section which is completely or partially transparent allows for visualization of radiopaque marker bands placed on the catheter shaft underneath the balloon, thereby facilitating assembly of the balloon catheter. Preferably, the transparent sections are at or adjacent to the ends of the working length of the balloon or centrally located along at least a section of the working length, to facilitate radiopaque marker visualization. However, transparent section(s) of the balloon can be provided at a variety of desired locations on the balloon, including extending the entire working length or the entire length of the balloon.

The medical device component of the invention is at least in part transparent due to the fluid applied to the otherwise opaque material forming the component. The increased transparency of the component such as a catheter balloon facilitates assembly of the catheter by allowing for visualization through the balloon of radiopaque markers on the catheter shaft. Additionally, the markers can be visualized during stent placement on the balloon and as a result would also be facilitated by the present invention because the stent could be accurately positioned with respect to the markers. These and other advantages of the invention will become more apparent from the following detailed description when taken in conjunction with the accompanying exemplary drawings.

BRIEF DESCRIPTION OF THE DRAWINGS

FIG. 1 is an elevational view, partially in section, of a balloon catheter that embodies features of the invention, showing the balloon in an unexpanded state.

FIG. 2 is a transverse cross sectional view of the catheter of FIG. 1 taken along lines 2—2.

FIG. 3 is a transverse cross sectional view of the catheter of FIG. 1 taken along lines 3—3.

DETAILED DESCRIPTION OF THE INVENTION

As shown in FIGS. 1–3, the catheter 10 of the invention generally includes an elongated catheter shaft 11 having a proximal section 12 and distal section 13, an inflatable balloon 14 comprising a porous opaque material on distal section 13 of the catheter shaft 11. The catheter shaft 11 comprises an outer tubular member 19 and an inner tubular member 20 disposed within the outer tubular member and defining with the outer tubular member annular inflation lumen 21. Inflation lumen 21 is in fluid communication with interior chamber 15 of the inflatable balloon 14. The inner tubular member 20 has an inner lumen 22 extending therein, which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19. An adapter 17 mounted on the proximal section 12 of shaft 11 provides access to inflation lumen and guidewire lumen 22. The embodiment shown in FIG. 1, a stent 16 is disposed about the balloon 14, and proximal and distal radiopaque marker bands 26 are aligned with the proximal and the distal ends of the stent 16 on the catheter shaft 11. Heat shrunk collars 40 on balloon are provided for securing the balloon 14 to the catheter shaft. However, the balloon may be secured to the shaft by a variety of suitable means including adhesive.

In the embodiment illustrated in FIG. 1, the intravascular catheter 10 of the invention is an over-the-wire catheter, with the balloon 14 in an unexpanded state. Balloon 14 is formed of a porous opaque material, having transparent sections 30 formed according to a method which embodies features of the invention. In the illustrated embodiment, the transparent sections 30 are at the proximal and distal ends of the working length of the balloon. The porous material forming the balloon 14 has a first portion with a refractive index, and a second portion with a different refractive index.

The porous opaque material forming the balloon 14 has a first refractive index. One such presently preferred material is expanded polytetrafluoroethylene (ePTFE), which can be inflated from a straight tube and deflated to a tube of similar dimensions. The ePTFE typically has a pore size of about 15 $\mu$m to about 110 $\mu$m. In a presently preferred embodiment, the balloon 14 comprises a first layer of porous material such as ePTFE, and a second layer of a second material such as an elastomer (not shown). The elastomer layer, which is preferably an inner layer, provides elastic expansion to the balloon 14 so that the balloon deflates to substantially the original uninflated dimension. The ePTFE is preferably a film which is wrapped and heat fused to form a tubular balloon.

A method which embodies features of the invention to allow visualization through an opaque balloon generally comprises providing a porous opaque film, providing a fluid having a refractive index substantially similar to that of the film, and contacting the film with the fluid so that the fluid at least partially fills pores in the film. In a presently preferred embodiment, the fluid is applied after the film is formed into the component such as a tubular balloon, to facilitate providing the fluid on the desired section of the component. Alternatively, the fluid may be applied to the film before being formed into the component. In a presently preferred embodiment, the fluid has a refractive index of about 1.3 to about 1.55 and preferably about 1.35 to about 1.5. In one embodiment, the fluid having a refractive index similar to that of the ePTFE balloon 14 is a biomedical implant grade of silicone having a refractive index of about 1.402 to about 1.41 relative to water. The fluid may be placed into contact with the balloon 14 using a device containing the fluid. The balloon 14 may also be immersed into the fluid or sprayed with the fluid. A heat set step may be used after the fluid is applied to the porous material to harden the material in the pores, as for example, in the case of a silicone-based adhesive which can be cured at room temperature or cured at elevated temperature for faster curing. The fluid may be applied to the porous material in one application, or in several applications.

The sections 30 of the balloon 14 thus treated to be fully or partially transparent are rendered permanently transparent where the fluid does not significantly evaporate or change properties in the pores of the porous material. For example, a silicone-based adhesive permanently fills the pores of the porous material. Alternatively, the sections 30 may be temporarily transparent, for example, where the fluid evaporates relatively quickly from the pores. Isopropyl alcohol is preferred over ethyl alcohol for use as the fluid, due to the slower evaporation rates of isopropyl alcohol.

Once the sections 30 of the opaque balloon material becomes clear it is possible to view the radiopaque marker bands 26 on the catheter shaft 11 and accurately position the balloon with respect to the markers. With the radiopaque marker bands at the ends of the balloon working length, the balloon is secured to the shaft so that the proximal end of the balloon is secured to the outer tubular member 19 and the distal end of the balloon 14 is secured to the inner tubular member 20. In the embodiment of FIG. 1, having stent 16 mounted on the balloon for deployment within a patient's body lumen, the transparent sections 30 provide for improved stent retention by providing a tacky balloon surface which inhibits stent movement on the balloon 14.

Although illustrated as an over-the-wire catheter, a variety of suitable catheter configurations may be used, including rapid exchange catheters which generally have a distal guidewire port, a proximal guidewire port spaced a substantial distance from the proximal end of the catheter,.and a short guidewire lumen extending between the proximal and distal guidewire ports.

The invention has been described in terms of preferred embodiments, however, certain modifications may be made without departing from the scope of the invention. Moreover, although individual features of embodiments of the invention may be shown in some of the drawings and not in others, those skilled in the art will recognize that individual features of one embodiment of the invention can be combined with any or all the features of another embodiment.

What is claimed is:

1. A method for visualization through a medical device component formed of a porous opaque film, the porous opaque film comprising a material having a first refractive index, comprising
   a) providing a fluid having a second refractive index substantially similar to the first refractive index; and
   b) applying the fluid to the film so that the transparency of the film is increased.

2. The method of claim 1 wherein the medical device component is a catheter balloon, and applying the fluid comprises introducing the fluid into pores of the film.

3. The method of claim 1 wherein the film comprises expanded polytetrafluoroethylene, and including selecting the fluid to have a refractive index within about 5% to about 20% of the refractive index of the film.

4. The method of claim 1 wherein the fluid is selected from the group consisting of an alcohol, propyl alcohol, and silicone, and wherein applying the fluid comprises exposing the film to the fluid by a method selected from the group consisting of spraying and immersing.

5. The method of claim 2 including securing the balloon to an elongated tubular catheter shaft.

6. The method to claim 5 wherein the shaft has radiopaque markers on a distal section thereof and wherein the balloon has a working length with a proximal end and a distal end, and including aligning the radiopaque markers at locations corresponding to the proximal and distal ends of the working length by visualizing through the balloon at least one radiopaque marker on the shaft.

7. The method of claim 5 wherein the shaft has radiopaque markers on a distal section thereof and wherein a stent is disposed about the balloon, the stent having a proximal end and a distal end, and including aligning the radiopaque markers at locations corresponding to the proximal and the distal ends of the stent by visualizing through the balloon at least one radiopaque marker on the shaft.

8. A catheter component comprising a porous material having a first portion with pores having air in the pores, the air having a first refractive index, and a second portion with pores having a material in the pores, the material in the pores having a second refractive index different from the first refractive index.

9. The catheter component of claim 8 wherein the first portion is opaque and the second portion has increased transparency relative to the first portion.

10. The catheter component of claim 8 wherein the second refractive index of the material in the pores is substantially similar to a refractive index of the porous material.

11. The catheter component of claim 8 wherein the porous material comprises expanded polytetrafluoroethylene, and the material in the pores has a refractive index within about 5% to about 20% of the refractive index of the expanded polytetrafluoroethylene.

12. The catheter of claim 8 wherein the material in the pores is selected from the group consisting of alcohol, propyl alcohol, and silicone.

13. The catheter component of claim 8 wherein the component comprises a balloon.

14. A catheter component, comprising a porous material having a first refractive index, with at least a section of the component having a material in pores of the porous material, the material in the pores having a second refractive index substantially similar to the first refractive index, so that the at least a section of the component is at least partially transparent.

15. A balloon catheter, comprising:
   a) an elongated tubular shaft having proximal and distal sections;
   b) a balloon comprising a porous material, the balloon having a first portion with pores having air in the pores, the air having a first refractive index, and a second portion with pores having a material in the pores, the material in the pores having a second refractive index different from the first refractive index.

16. The balloon catheter of claim 15 wherein the porous material is expanded polytetrafluoroethylene.

17. The balloon catheter of claim 15 wherein the second refractive index of the material in the pores of the porous material is substantially similar to a refractive index of the porous material, and is selected from the group consisting of alcohol, propyl alcohol, and silicone.

18. The balloon catheter of claim 15 wherein the shaft has radiopaque markers on a distal section thereof and wherein the balloon has a working length with a proximal end and a distal end, and wherein the radiopaque markers are aligned at locations corresponding to the proximal and distal ends of the working length.

19. The balloon catheter of claim 15 wherein the shaft has radiopaque markers on a distal section thereof and wherein a stent is disposed about the balloon, the stent having a proximal end and a distal end, and wherein the radiopaque markers are aligned at locations corresponding to the proximal and the distal ends of the stent.

20. A method of mounting an opaque balloon onto a catheter shaft comprising:
   a) providing an elongated catheter shaft with proximal and distal sections with at least one radiopaque marker on a location on the distal shaft section;
   b) disposing an opaque tubular balloon formed of a porous material having a first refractive index about the distal shaft section with the at least one marker on the distal shaft section being within an interior portion of the balloon;
   c) applying on the balloon a fluid having a second refractive index substantially similar to the first refractive index so that at least a portion of the balloon has increased transparency, so that the marker within the interior of the balloon can be visualized through the balloon; and
   d) securing the balloon to a location on the distal shaft section based upon the location of the marker on the distal shaft section.

* * * * *